(12) United States Patent
Berube et al.

(10) Patent No.: US 6,817,999 B2
(45) Date of Patent: Nov. 16, 2004

(54) FLEXIBLE DEVICE FOR ABLATION OF BIOLOGICAL TISSUE

(75) Inventors: Dany Berube, Milpitas, CA (US); Pierre-Antoine Chapelon, Fremont, CA (US)

(73) Assignee: AFX, Inc., Fremont, CA (US)

( * ) Notice: Subject to any disclaimer, the term of this patent is extended or adjusted under 35 U.S.C. 154(b) by 0 days.

(21) Appl. No.: 10/039,873

(22) Filed: Jan. 3, 2002

(65) Prior Publication Data

US 2003/0125730 A1 Jul. 3, 2003

(51) Int. Cl.[7] ............................................... A61B 18/18
(52) U.S. Cl. ..................................... 606/41; 604/95.04
(58) Field of Search ........................... 601/2; 604/95.01, 604/95.04, 525, 528; 606/32, 41, 45, 47; 607/98, 101

(56) References Cited

U.S. PATENT DOCUMENTS

| | | | |
|---|---|---|---|
| 5,603,697 A | * 2/1997 | Grundy et al. | ................. 604/95 |
| 5,755,760 A | 5/1998 | Maguire et al. | |
| 5,823,955 A | 10/1998 | Kuck et al. | |
| 5,871,525 A | * 2/1999 | Edwards et al. | ............. 607/104 |
| 5,921,924 A | 7/1999 | Avitall | |
| 6,090,104 A | 7/2000 | Webster, Jr. | |
| 6,102,886 A | * 8/2000 | Lundquist et al. | ............. 604/22 |
| 6,245,062 B1 | 6/2001 | Berube et al. | |
| 6,277,113 B1 | 8/2001 | Berube | |
| 6,471,696 B1 | * 10/2002 | Berube et al. | ................. 606/33 |
| 6,514,246 B1 | * 2/2003 | Swanson et al. | ............... 606/41 |
| 6,517,568 B1 | * 2/2003 | Sharkey et al. | ................ 607/96 |

FOREIGN PATENT DOCUMENTS

EP                1118310             1/2001

OTHER PUBLICATIONS

Gauthier et al, "A Microwave Ablation Instrument With Flexible Antenna Assembly And Method" U.S. patent application No. 09/484,548 filed Jan. 18, 2000.
Dany Berube, "Electrode Arrangement for Use in A Medical Instrument," U.S. patent application No. 09/548,331, filed Apr. 12, 2000.
Mody et al "A Tissue Ablation and Apparatus with a Sliding Ablation Instrument and Method," U.S. patent application No. 09/751,472, filed Dec. 28, 2000.

* cited by examiner

Primary Examiner—Michael Peffley
Assistant Examiner—Aaron Roane
(74) Attorney, Agent, or Firm—Fenwick & West LLP

(57) ABSTRACT

An ablation system incorporating an enhanced deflectable distal portion, is provided. The system includes an elongated tubular member having a deflectable distal portion adapted to assume a specific predetermined or predefined shape when deployed. The predetermined shape allows for the creation of a desired uniform energy emission pattern with respect to a target tissue, such that energy may be directed toward the target tissue independent of an approach orientation of the ablation system. The energy pattern results in the creation of a desired tissue ablation. The ablation system may further comprise a steering system which aides in directing the distal portion toward a target tissue site. The steering system may alternatively be incorporated into a separate guiding catheter as part of the ablation system.

9 Claims, 17 Drawing Sheets

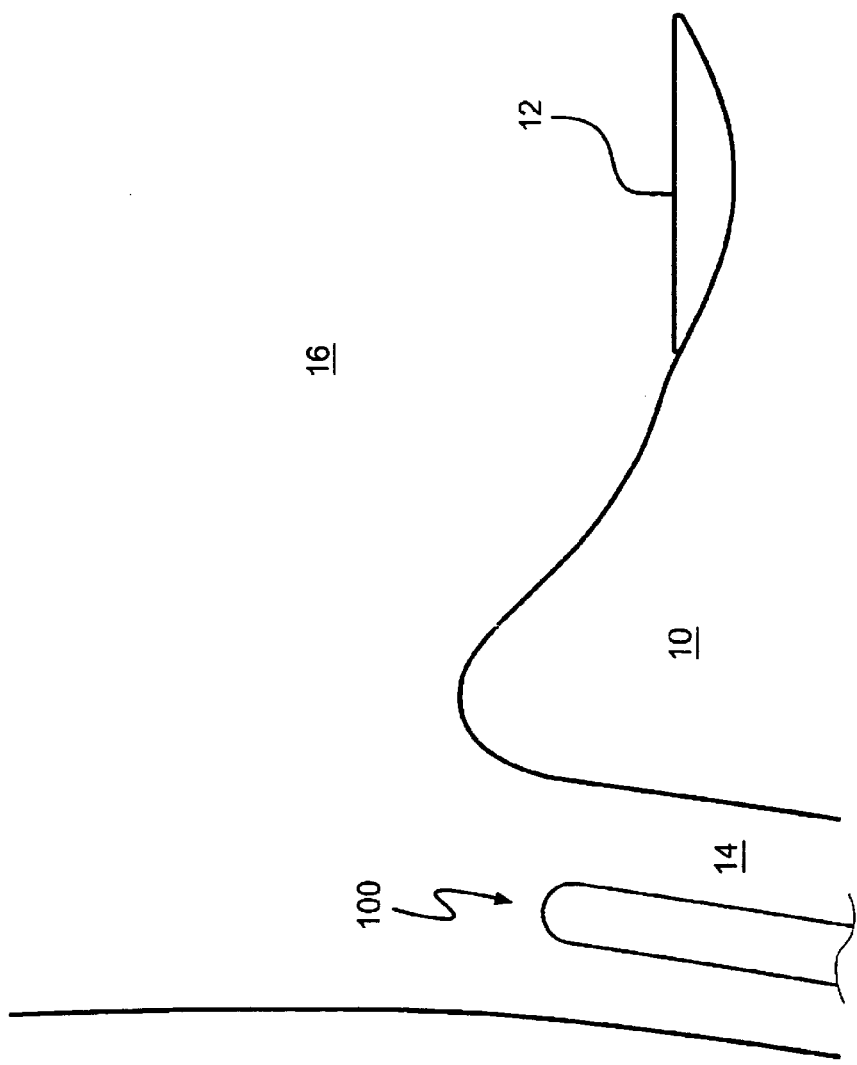

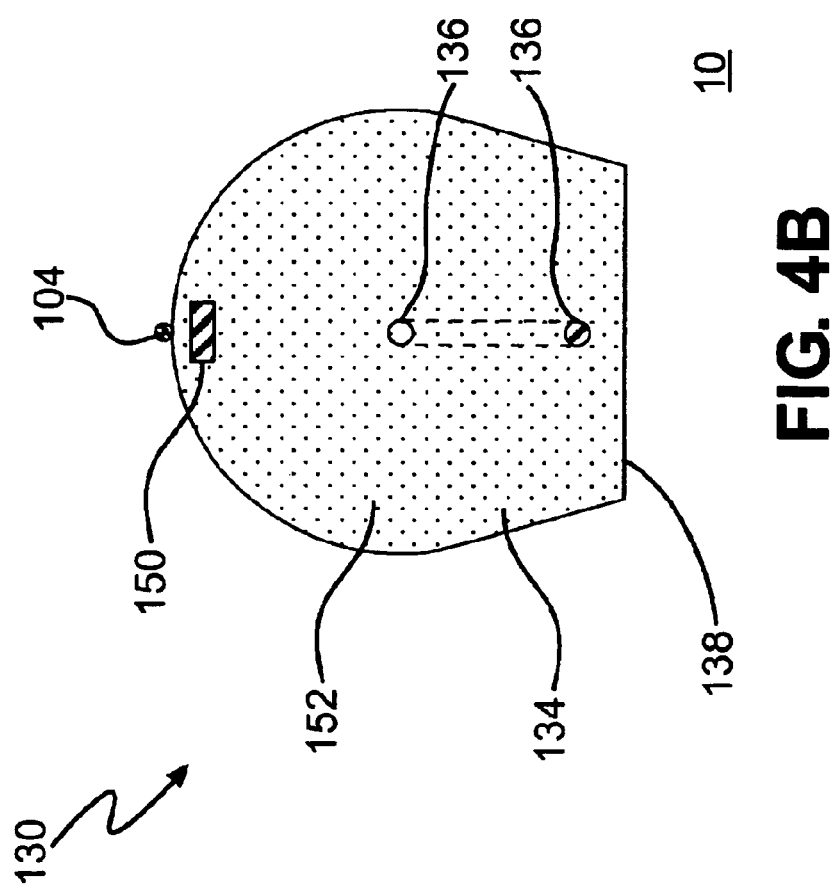

FLEXIBLE DEVICE FOR ABLATION OF BIOLOGICAL TISSUE

BACKGROUND OF THE INVENTION

1. Field of Invention

The present invention relates generally to catheter systems used in diagnosis and treatment of various body tissues and, more specifically, to ablation systems for ablating cardiac tissue in the treatment of electrophysiological diseases.

2. Description of the Related Art

As is well know, catheters provide medical professionals access to various interior regions of the human body in a minimally invasive manner. In such a way, catheters are tremendous medical tools in support of diagnosis and treatment of different tissues of the body. Catheters allow such professionals to place one or more medical instruments, pharmacological agents or other matter at a target tissue site. For example, in cardiac procedures in support of diagnosis and treatment of atrial fibrillation, catheters provide access to various chambers of the heart, carrying ablation devices which translate therein to such sites for ablation of specific cardiac tissue associated with atrial fibrillation.

Ablation of tissue, cardiac tissue for example, is typically directly related to the orientation of the ablation element, from which energy sufficient to ablate biological tissue is emitted, with respect to a target tissue site. For such procedures, precise control of the ablation device is desirable to ensure proper placement of the ablation element utilized in creation of one or more desired lesions. As an electrophysiologist, or other medical professional, manipulates the proximal end of the catheter system, the distal end of the catheter must be responsive to such movement in a very predetermined, smooth-flowing and proportional way.

Additionally, the orientation of the ablation device, from which ablative energy is emitted and directed toward the target tissue, differs with the modality utilized for the procedure. For example, with tip electrode RF based devices, the tip must be properly placed in direct contact with the target tissue. For creation of numerous intermediate lesions along a desired lesion path, the tip electrode must be moved across the target tissue surface in a controlled fashion, which is often difficult due to inconsistencies of the tissue surface. Under certain conditions, the tip may act to impede movement across the surface of the target tissue, causing the tip to erratically jump or skip across the tissue in an undesirable way.

For example, for the treatment of atrial flutter, it is often desirable to ablate the isthmus which lies between the inferior vena cava and the tricuspid valve. The contour of this tissue, while generally curvilinear, is irregular and inconsistent, comprising various peaks and valleys, which differ from individual to individual. Ablating tissue in this region often requires the precise and controlled placement of the distal tip of the ablation device. Because of the curvilinear nature of the isthmus, it has been found to be difficult to lay down a straight long linear ablation element to ablate this area. This task is complicated by the fact that the steering or guiding system of the ablation system typically directly impacts the approach and orientation of the tip upon the tissue, which further impairs the ability of the system to transmit sufficient ablative energy for proper tissue ablation. Furthermore, due to the desired depth of the ablation required at this location, proper placement of the ablation device is critical to the creation of a desired long continuous deep lesion therein.

Proper placement of an ablation device is also exasperated by the fact that some ablative energy technologies require energy transmission conduits which are bulky, or otherwise constructed from materials less flexible, making the distal portion of the catheter difficult to properly position. For example, distal portions of optical fiber or microwave based ablation systems, or catheter systems comprising an endoscopic device, may be more difficult to maneuver due to the lack of flexibility in the transmission mediums utilized therein. As should be readily apparent, when the distal portion of an ablation catheter system is not properly positioned, ablative energy is not properly directed and applied to the target tissue, resulting in poor lesion formation. It is therefore essential that the ablative device be able to be manipulated and sufficiently controlled to be properly positioned to transfer the requisite energy to ablate biological tissue and create a desired lesion therein.

SUMMARY OF THE INVENTION

Accordingly, it is a general object of the present invention to provide an ablation system which resolves the above-identified problems. Another object of the present invention is to provide an ablation system which ensures proper placement of an ablation device upon a target tissue to be ablated. Yet another object of the present invention is to provide an ablation system incorporating a deflectable ablative device which can emit a relatively uniform energy pattern therefrom. Another object of the present invention is to provide an ablation system to ablate tissue, forming a lesion therein which is substantially independent of an azimuth or approach angle. Still another object of the present invention is to provide an ablation system to easily and effectively ablate the isthmus between the inferior vena cava and the tricuspid valve without the need for a precise deflection system. Yet another object of the present invention is to provide a catheter system which ensures proper placement of an ablation device proximate a target tissue site during creation of a long continuous lesion.

These and other objects are achieved through systems disclosed herein. More specifically, a system for ablating a selected portion of biological tissue at a target tissue site is provided. The system is particularly suitable to ablate cardiac tissue, as well as other soft tissues of the body, and includes a tubular member having a distal end including an ablative device which, in turn, includes one or more ablation elements adapted to emit ablative energy therefrom, and a steering system operably attached to a proximal section. The distal end of the tubular member is configured to be deflected into a predetermined geometric shape wherefrom a relatively uniform energy pattern is emitted, such that tissue ablation can occur substantially independent from an approach angle defined between the tubular member and the target tissue surface. In this way, for example, with a substantially side-firing ablation device one could bend or otherwise deflect the ablation device into a specific shape to obtain a uniform energy distribution about the distal end of the ablation device.

In one embodiment, the ablation device includes at least one ablation element adapted to emit ablative energy therefrom. The ablation device is configured to engage tissue from one of many approach angles while maintaining proper ablative energy transfer to the tissue resulting in tissue ablation and the creation of one or more desired lesions.

In another embodiment, the ablation device includes at least one flexible ablation element adapted to emit ablative energy therefrom. The at least one ablation element is configured to deflect along with the tubular member. Alternatively, the ablation device may include at least one ablation element having a geometric configuration which allows deflection of the distal end of the ablation device.

In still another embodiment, the ablation device may also include a shielding means adapted to be opaque with respect to the corresponding ablative energy utilized, protecting tissues surrounding a target tissue site from the ablative energy. Additionally, the shielding means may be configured to reflect at least a portion of the ablative energy toward the target tissue site to facilitate or encourage tissue ablation and lesion formation.

In still another embodiment, the tubular member of the ablation device translates within a tubular guiding member, the distal portion of the ablation device is adapted to include a preformed shape. As the ablation device emerges from the distal opening of the guiding member, the distal portion assumes its preformed curvilinear shape. The preformed shape may be selected to facilitate the emission of a uniform energy pattern therefrom.

In another embodiment, the ablation device is a catheter system wherein the tubular member is elongated to facilitate entry into a patient's vascular system and advancement to a target tissue site, a cardiac muscle site for example.

The ablative energy is preferably electromagnetic energy in the microwave range. However, other suitable tissue ablation energies include, but are not limited to, cryogenic, ultrasonic, laser, chemical and radiofrequency.

In yet another embodiment, the ablation device is a microwave antenna assembly which includes an antenna configured to emit microwave ablative energy. The ablation device may also include a shielding means coupled to the antenna assembly. The shielding means may be adapted to substantially shield a surrounding area of the antenna from the electromagnetic field radially generated therefrom while permitting a majority of the field to be directed generally in a predetermined direction toward the target tissue site. Alternatively, the shielding means, in another embodiment, may be adapted to absorb the electromagnetic energy transmitted therefrom protecting surrounding tissues. The ablation device may further include an insulator which functions to hold the shielding means and antenna in fixed relationship with respect to each other and a target tissue site, further controlling the ablative characteristics of the ablation device.

In yet another embodiment, the steering system is part of an elongated guiding member having at least one lumen passing therethrough, the tubular member of the catheter translating therein.

In another aspect of the present invention, a method for treatment of a Heart includes entering the ablative device into a patient's vasculature; guiding the distal end of the ablation device into a chamber of the patient's heart; manipulating the ablation device until the distal end is proximate a target tissue site; applying ablative energy from an energy source to the ablation device.

In one embodiment, the manipulating is performed by incrementally advancing the ablative device along a plurality of positions along an ablation path to produce a substantially continuous lesion.

In another embodiment, the step of manipulating is performed by incrementally sliding, or otherwise moving, the ablative device along a predefined ablation path to produce a long and substantially continuous lesion.

In yet another embodiment, the step of sliding includes the step of positioning the ablative device in an overlapping arrangement with respect to prior ablation sites along the ablation path.

Other objects and attainments together with a fuller understanding of the invention will become apparent and appreciated by referring to the following description and claims taken in conjunction with the accompanying drawings.

BRIEF DESCRIPTION OF THE DRAWINGS

FIGS. 2A–E are side views of an ablation system being deployed, in accordance with the present invention.

FIG. 4B is an end view of the ablation system of FIG. 4A.

DETAILED DESCRIPTION OF THE INVENTION

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims.

Figure 1A:
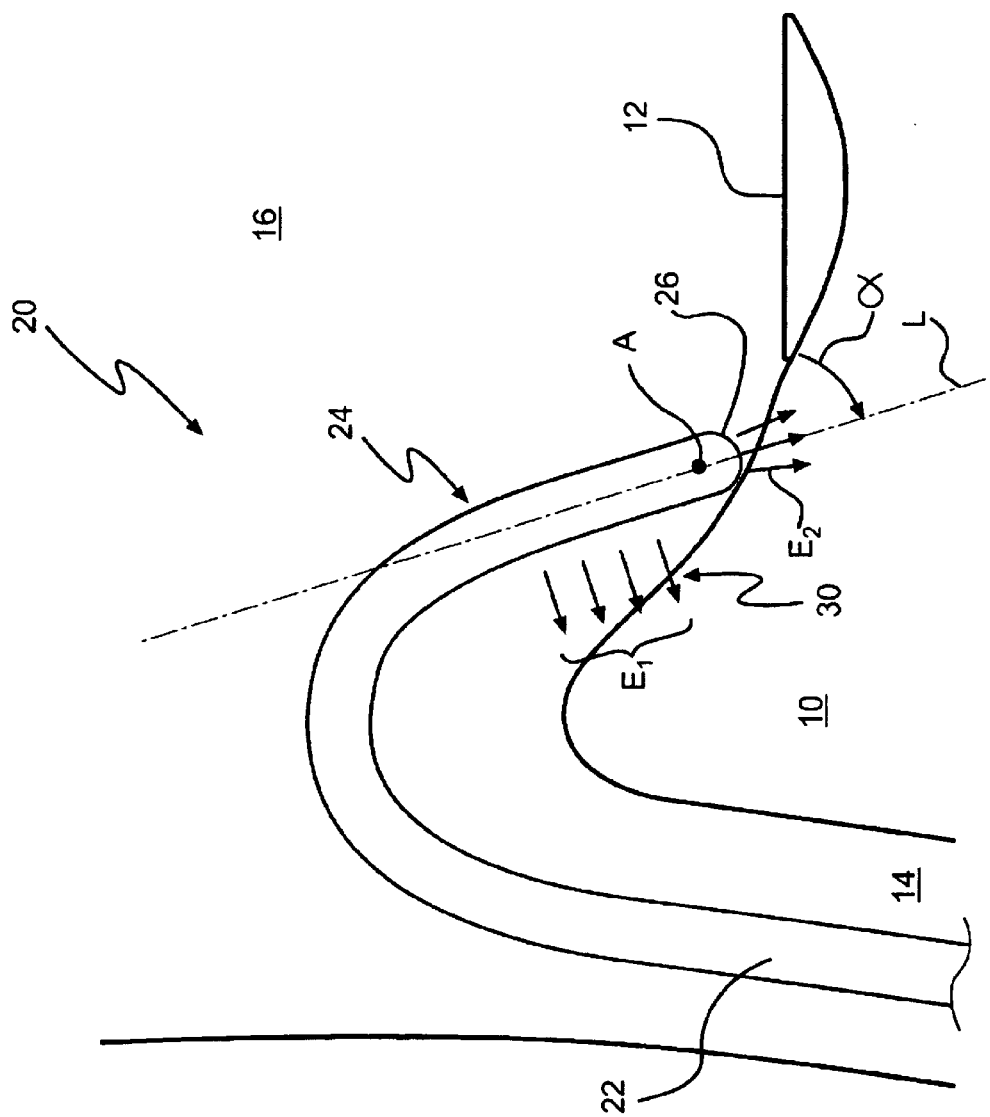
FIG. 1A is a side view of an ablation system.

Turning to FIG. 1A, a catheter 20 known in the art will be discussed. More specifically, FIG. 1A depicts catheter 20 advanced from a point proximate to the femoral vein (not shown), through the inferior vena cava 14 (IVC), and into the right atrium 16, a distal tip 26 of catheter 20 engaging cardiac tissue 10, between the IVC 14 and tricuspid valve 12. For purposes of clarity, the depiction of the cardiac structure has been simplified.

The catheter 20 comprises a long tubular member 22 having a proximal portion (not shown) and distal portion 24, the proximal portion operably attached to a handle portion (not shown). The distal portion 24 includes, or otherwise incorporates, an ablation device 30 including one or more ablation elements. The one or more ablation elements are arranged and configured to emit ablative energy in a direction generally away from an emission surface of the catheter 20 body, a portion of the radiating energy pattern generally designated by the arrows $E_1$ and $E_2$, and the emission surface corresponding to the outer catheter surface from which the energy is emitted, directly or indirectly, with respect to catheter 20.

As should be readily apparent, the emission surface may comprise the surface of one or more ablative elements embedded thereon, such as one or more electrodes adapted to contact target tissue and emit thermally conductive ablative energy. Alternatively, one or more ablative elements may be encased within the ablation device itself, the catheter structure allowing a substantial portion of the ablative energy to pass therethrough and engage target tissue. Such a system has the additional advantage, especially when the material within which the ablative elements are encased absorbs substantially none of the ablative energy which passes therethrough, of not charring or adhering to the target tissue, or causing other tissue damage generally associated with thermal conduction based systems.

The steering system of catheter 20 typically comprises at least one pull wire operably attached to a control means as part of the handle portion (not shown) and the distal portion 24 at an attachment point A. Operation of the control means results in the deflection of distal portion 24 of catheter 20. Since the attachment point A is close to the distal end 26 of distal portion 24 it is often difficult for an operator, an electrophysiologist for example, to manipulate the distal portion 24 in such a way as to position the emitting surface substantially proximal and parallel to cardiac tissue 10 in order to create a desired lesion therein. As depicted in FIG. 1A, with an improperly positioned distal portion, a substantial portion of the ablative energy fails to effectively engage tissue 10. Rather, the energy $E_1$ is absorbed in the blood.

As further depicted in FIG. 1A, when a portion of distal end 26 engages tissue 10, an approach angle $\alpha$ is defined between a longitudinal axis line L of catheter 20 which passes through attachment point A and the surface of tissue 10. Certain catheter systems may have distal energy delivery or ablation elements which are adapted to deliver an energy pattern from the distal end of the system toward a target tissue, distal end 26 toward tissue 10 for example, as depicted by arrows $E_2$. As should be readily understood, when catheter 20 is positioned as shown in FIG. 1A, distal end 26 is not effectively placed perpendicularly in contact with tissue 10. Thus, tip-firing energy $E_2$, like energy $E_1$, is not effectively transmitted to tissue 10, resulting in poor ablation formation therein. Therefore, when approach angle $\alpha$ is about 0°, energy $E_1$ is most effectively transmitted to tissue 10. Conversely, when approach angle $\alpha$ is about 90°, energy $E_1$ is most effectively transmitted to tissue 10.

It is important to note that energy patterns $E_1$ and $E_2$ are generic in the sense that they do not depict energy patterns of ablation systems which require direct contact with the target tissue. However, as is discussed in more detail below, use of such systems is enhanced through the addition of structures and methods in accordance with the present invention. For example, if distal tip 26 of catheter 20 included an electrode which required direct contact with target tissue 10, such a device would be difficult to maneuver and manipulate in such a way as to create numerous intermediate lesions as part of a long continuous lesion, especially during a beating heart procedure.

Figure 1B:
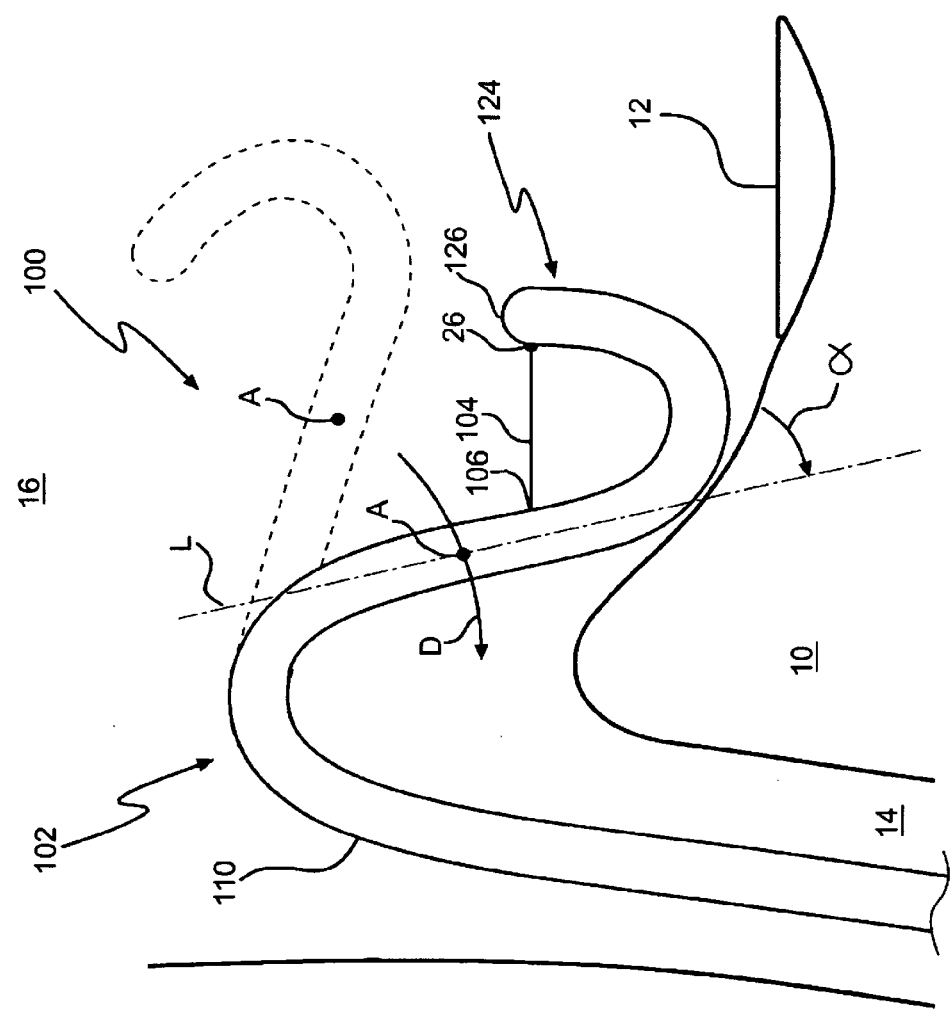
FIG. 1B is a side view of an ablation system including a flexible distal portion in accordance with the present invention.

Now turning also to FIG. 1B, a catheter 100 in accordance with the present invention is shown. As depicted in FIG. 1A with respect to catheter 20, catheter 100 is shown passing through the inferior vena cava 14 and entering the right atrium 16. Catheter 100 comprises an elongated tubular body member 110 which leads to a distal portion 124, and finally a distal end 126. Distal portion 124 comprises an ablation device 130 (not shown) including one or more ablation elements 136 (not shown) adapted to emit ablative energy therefrom toward a target tissue site.

Figure 1C:
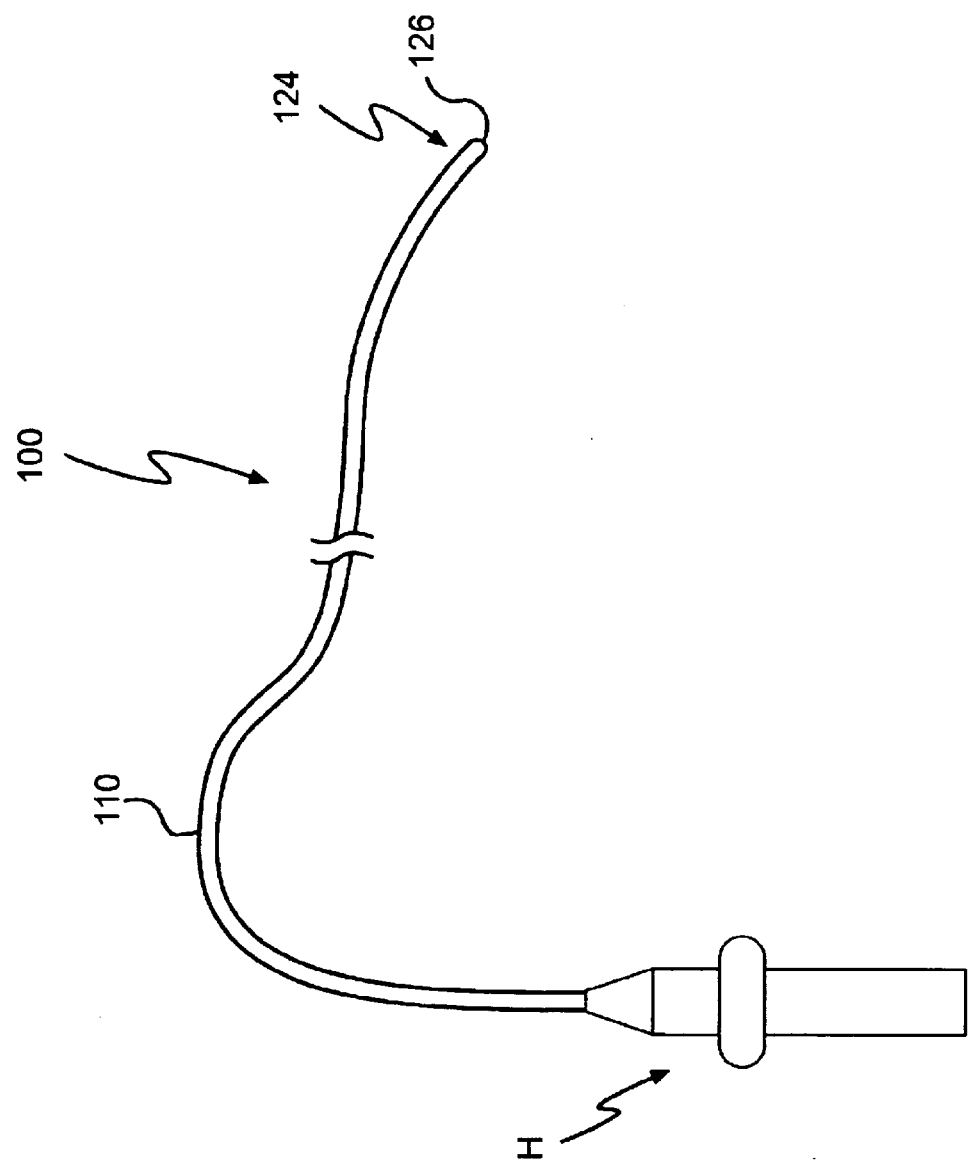
FIG. 1C is another side view of the ablation system in accordance with the present invention.

Catheter 100 further incorporates a steering system 102 having a distal attachment point A located proximal to distal portion 124 and a proximal attachment point at handle H as shown in FIG. 1C. As is discussed in greater detail below, once distal portion 124 is within the right atrium, tension is applied to a pull wire 104 which acts to deflect portion 124 substantially as shown. Therefore, as should be readily apparent from FIG. 1B, as the catheter 100 is deflected by steering system 102 from an initial position (shown in dashed line), with point A moving in a direction indicated by arrow D, the portion of catheter 100 distally located from point A is directed toward at least a portion of target tissue 10. Such a configuration enables the distal portion 124 of catheter 100 to be placed proximal to target tissue 10, allowing the emitted energy pattern E adjacent the point of contact to effectively impact upon target tissue 10, ensuring proper lesion formation at that location.

As shown, when the distal portion 124 engages tissue 10, angle $\alpha$ is defined by the longitudinal axis line L of catheter 100 which passes through attachment point A and tissue 10. The overall flexibility of distal portion 124 is sufficiently greater than tubular member 110, such that translation of pull wire 104 results in the deflection of portion 124 with respect to tubular member 110, which substantially retains its form.

Thus, it should be apparent that such a catheter system 100 is much less dependent on the approach angle $\alpha$ for proper lesion formation adjacent the point of contact between catheter 100 and tissue 10, unlike catheter 20 discussed above. Moreover, the distal portion 124 can be preformed or deflected to take on a curvilinear shape allowing ablation systems which require direct contact with the target tissue to be more easily moved in a controlled manner about the surface of the target tissue. For example, if one or more electrodes are placed along the distal portion 124, one or more of the electrodes may be energized at any given time during movement of distal portion 124 about tissue 10. Such a system offers better control and performance with respect to tip electrode systems which rely on moving the tip itself across the surface of the tissue.

As will be discussed in more detail below, steering system 102 may be incorporated into a separate guiding catheter (not shown), such that the ablation catheter, having an ablation device, can translate therein. It should also be noted that while the ablation device may be described as being deflected through operation of pull wire 104, this does not necessarily mean the orientation of the ablation device is straight or linear. For example, the ablation device may be curved to address the natural curvature of an internal organ or to assist in its proper placement, the ablation device directed to the target tissue through the use of a guiding catheter configured to restrict the ablation device to an orientation similar to the guiding catheter until the ablation device emerges and assumes its predetermined form.

The ablation device may also incorporate a shielding means adapted to be opaque with respect to the corresponding ablative energy utilized, protecting surrounding tissues from the ablative energy. Additionally, the shielding device may be adapted to reflect at least a portion of ablation energy toward the target tissue site.

Steering system 102 may be any suitable steering system able to properly deflect catheter 100 to achieve the desired ablations described herein. Such steering systems are disclosed in commonly owned and co-pending U.S. Patent Application entitled, "Catheter Having Improved Steering," filed concurrently with the present application and hereby incorporated herein, in its entirety.

Additionally, it should be noted that while the pull wire 104 is shown traveling outside the catheter 100 structure, proximate to distal portion 124, the distal portion 124 may comprise a lumen (not shown) ending near the distal tip through which the pull wire 104 can translate. The lumen would be adapted to minimize frictional forces between itself and pull wire 104 as well as provide attachment point DA at a distal end of the lumen near tip 126. In this way, all components of catheter 100 may be encased within the catheter itself.

In operation, catheter 100 is steered, or otherwise directed, through the operation of steering system 102. Since the steering system 102 is operably attached at point SA along catheter 100, the catheter 100 structure distal to point SA remains substantially unaffected by catheter steering. As is discussed in greater detail below, with reference momentarily to FIG. 4A, once the distal portion 124 is directed toward a target area within the patient, within the right atrium for example, distal portion 124 is further deflected through operation of pull wire 104.

Figure 2B:
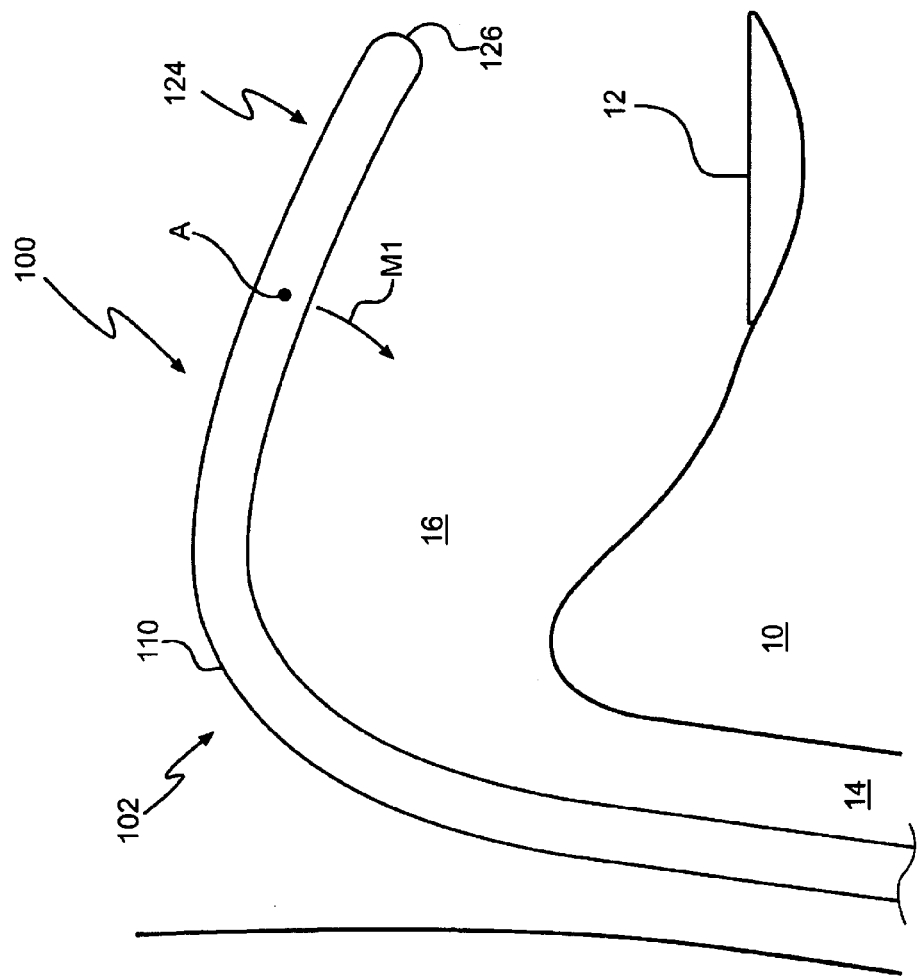

Now turning to FIGS. 2A–2E, the operation of catheter system 100 can be more readily understood. While FIGS. 2A–2E depict the ablation, or otherwise medical treatment, of the isthmus between the inferior vena cava (IVC) 14 and tricuspid valve 12, it should be apparent that such a system 100 can be utilized in other areas of the body or in association with other bodily organs, such as the bladder or stomach. As shown in FIG. 2A, catheter 100 is depicted advancing percutaneously from a point proximal to the IVC 14, the femoral vein for example, toward the target tissue site.

Now referring specifically to FIG. 2B, as the distal portion 124 of catheter 100 enters the right atrium 16, the steering system 102 acts to deflect distal portion 124 and direct distal tip 126 in a direction generally toward the tricuspid valve 12. As is depicted, and as should be readily understood, once the distal portion 124 is within the right atrium, the catheter 100 is typically no longer advanced, however, distal portion 124 is continually deflected by operation of the steering system 102, as described in greater detail above. Continued operation of the steering system 102 results in further deflection of distal portion 124 with respect to the catheter member 110, attachment point A moving generally in a direction noted by arrow M1.

Figure 2C:
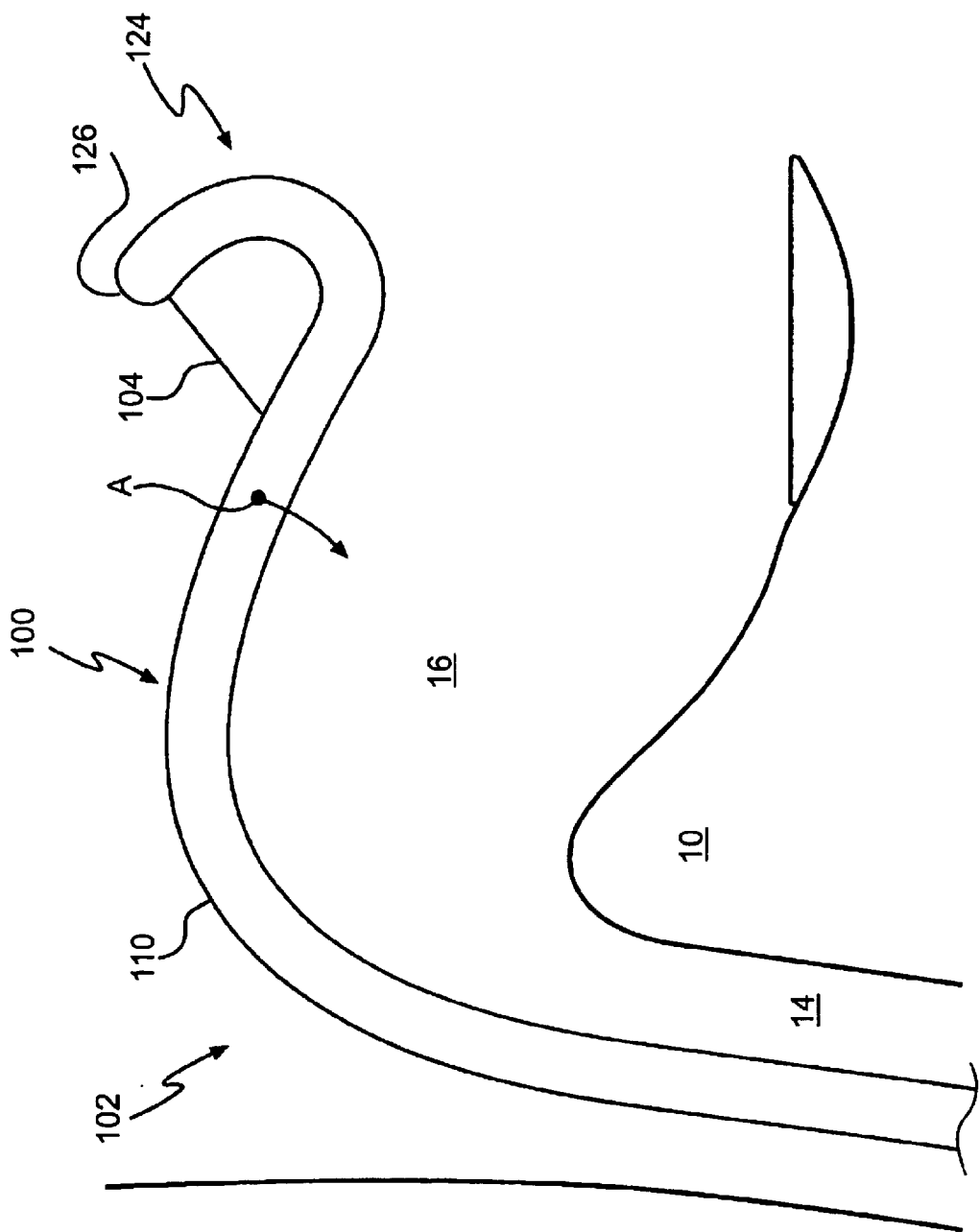
Figure 2D:
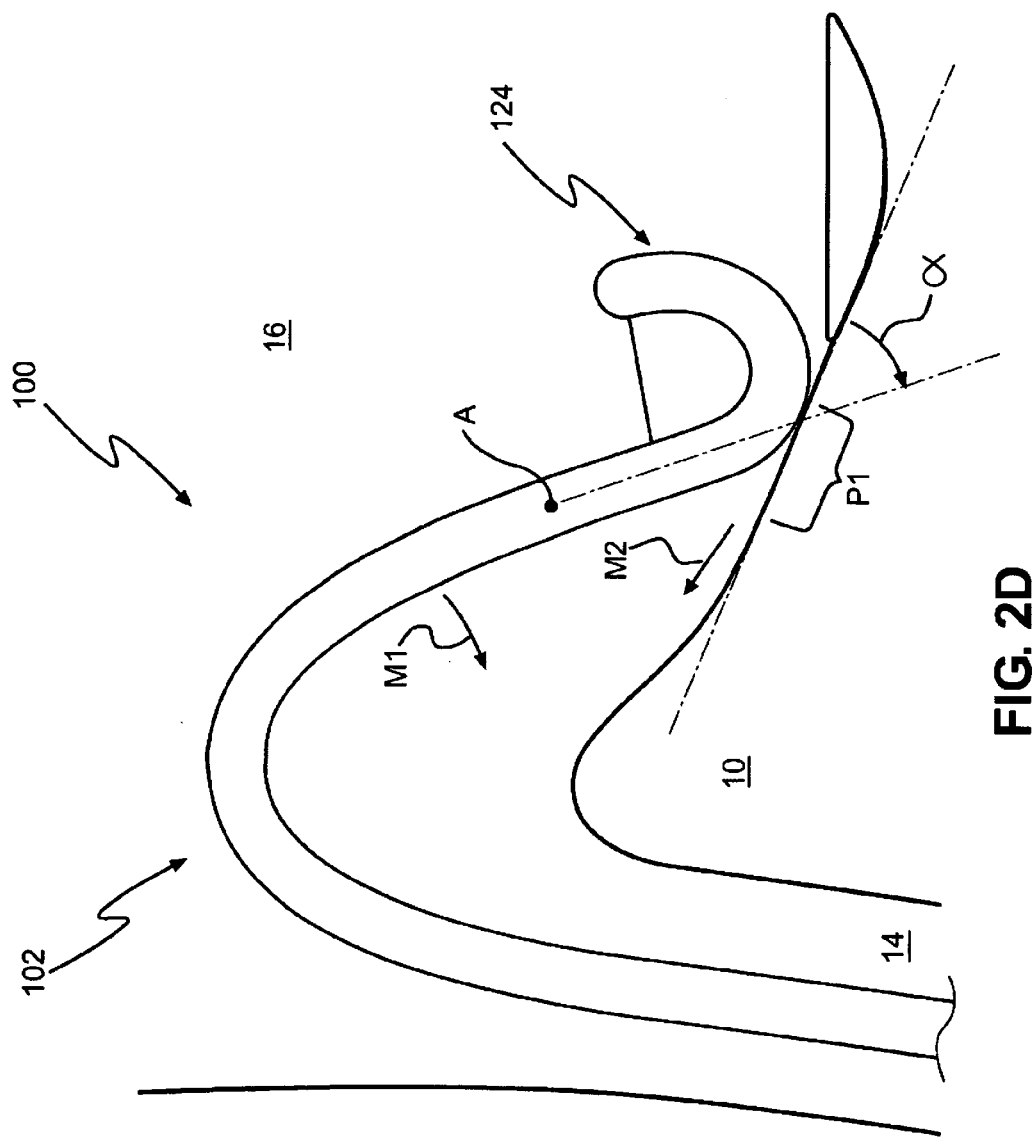

With reference also to FIG. 2C, once the distal portion 124 lies within the atrium 16, the distal portion 124 is deflected through translation of the pull wire 104, as described in greater detail above. Once the distal portion 124 is deflected the desired predetermined amount, approximately 180° as shown for illustration purposes only, the distal portion is further directed towards target tissue through continued operation of steering means 102, as depicted in FIG. 2D. The distal portion 124 is steered, or otherwise further manipulated, until the a portion of the distal portion 124 is positioned proximate the target tissue 10, indicated by position P1. As discussed above, irregardless of the approach angle α, with the distal portion 124 positioned as shown, ablative energy impinges upon target tissue 10 to create a first ablation and corresponding lesion at position P1.

Figure 2E:
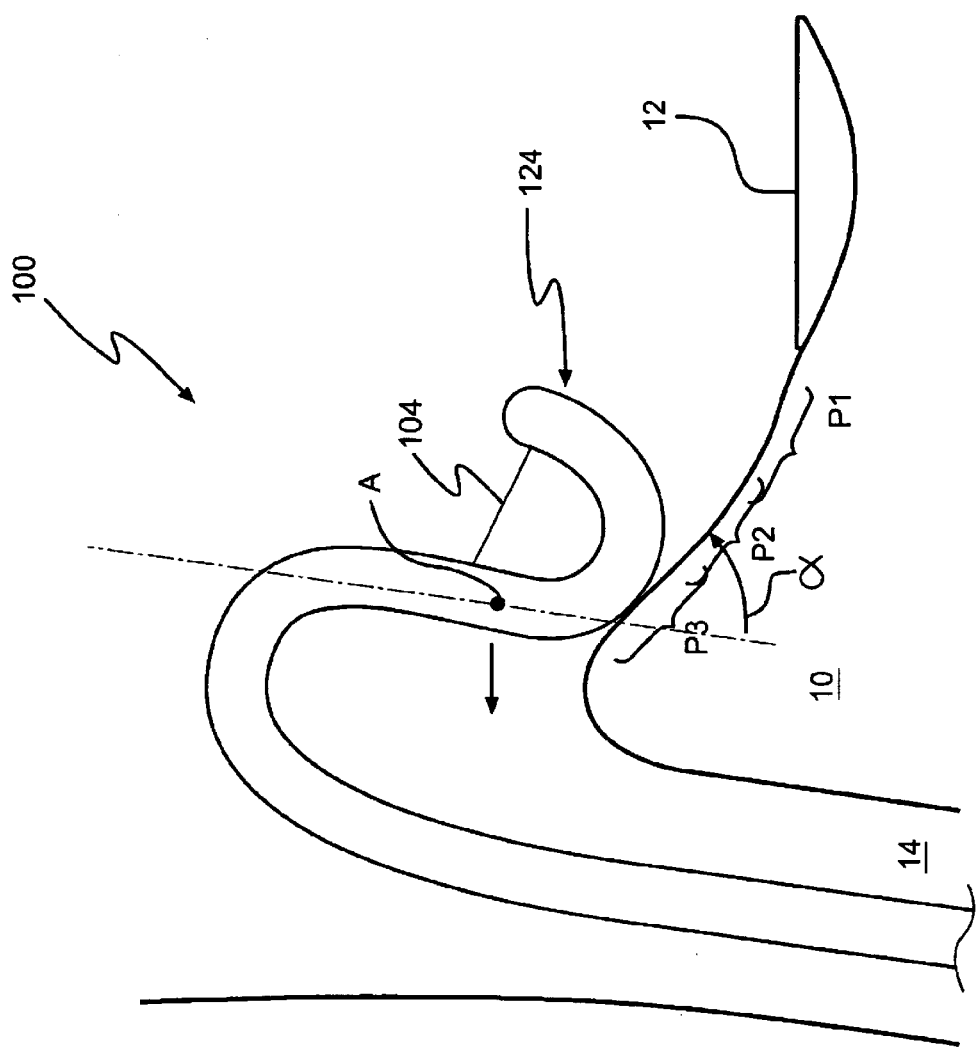

Once the first ablation is complete, further operation of steering means 102 results in the distal portion 124 moving in a direction generally depicted as M2 along tissue 10 until a second position is reached, indicated by position P2 as shown in FIG. 2E. Additionally, once the ablation at position P2 is complete, the distal portion 124 is further advanced as described above until a position P3 is reached.

Now with reference to FIGS. 3A–3C, another embodiment of an exemplary catheter system will be discussed. As depicted, catheter system 200 comprises a guiding catheter 201 having at least one lumen passing therethrough, and a steering system 202 operably attaching to guiding catheter 201 generally at the attachment point SA. Catheter system 200 further comprises an ablation catheter 204 which translates through the at least one lumen of the guiding catheter 201. Ablation catheter 204 comprises a deflection means for deflecting the distal portion 224 thereof. The deflection means may be any suitable means, such as the deflection means described above with reference to catheter system 100.

Preferably, the deflection means comprises a preformed or preshaped support member 250 encased within a portion of distal portion 224. Member 250, when no external forces are acting upon distal portion 224, acts to deflect distal portion 224 to its preformed or preshaped orientation. The flexibility of member 250 is somewhat less than that of guiding catheter 201, such that as the distal portion 224 exits the distal opening of catheter 201, distal portion 224 takes on the preformed shape of member 250, as is discussed in more detail below. Support member 250 may be formed having any suitable cross-sectional geometry including, but not limited to, circular, square, elliptical, or rectangular. For example, the cross-sectional geometry may be in the form of a rectangle limiting its deflection to the geometric plane passing through the longitudinal axis of the ablation catheter 204 during deflection of distal portion 224. In this way the distal portion 224 may be more precisely placed upon target tissue.

As with catheter system 100 discussed above, operation of catheter system 200 requires introduction of the catheter system into a patient's body, through the vasculature for example, and advanced until a distal portion is proximate target tissue to be ablated. Once the distal portion is in place, the catheter system 200 can be further manipulated to allow for ablation of the target tissue and formation of one or more desired lesions.

Figure 3A:
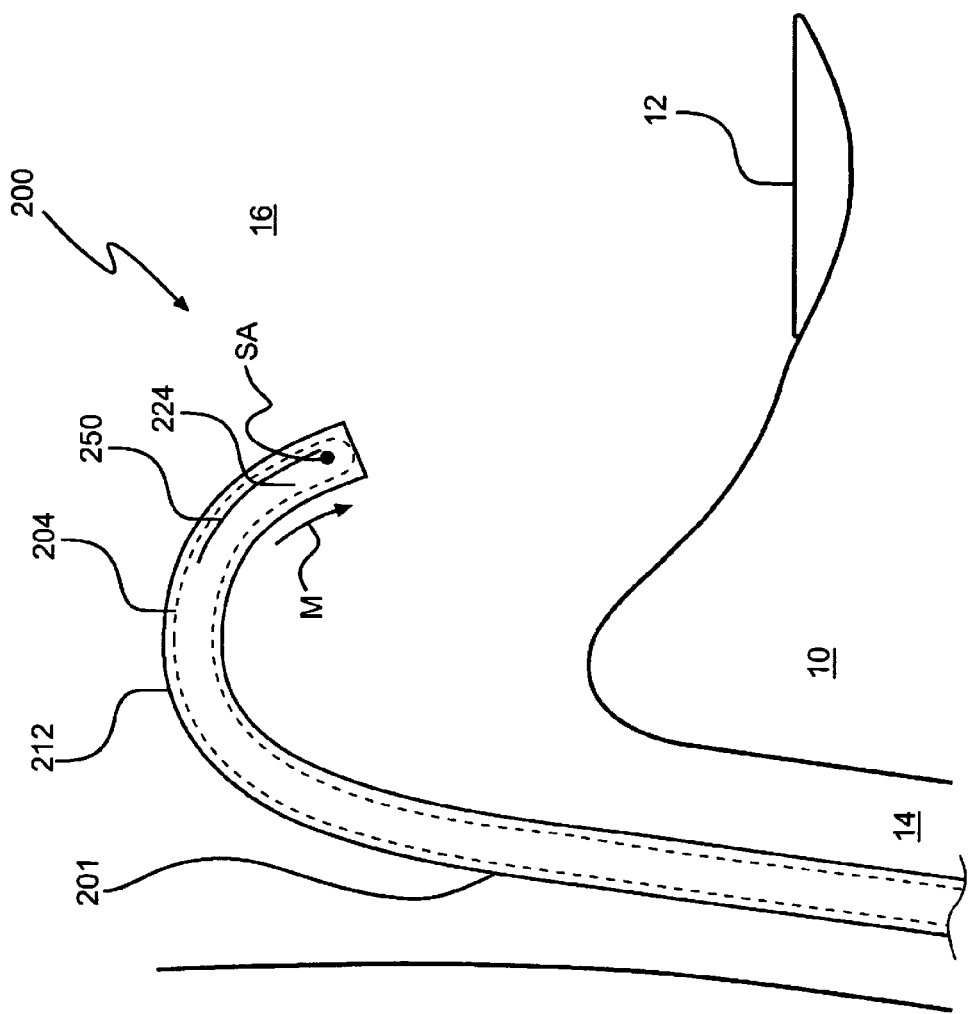
FIGS. 3A–C are side views of an alternative embodiment of an ablation system, in accordance with the present invention.

As shown in FIG. 3A, guiding catheter 201 of catheter system 200 is entered into the patient's vasculature, proximate to the femoral vein for example, and advanced into the IVC 14 until a distal portion 203 of catheter 201 is within the right atrium 16, substantially as shown. Once the guiding catheter 201 is properly placed, the ablation catheter 204 is translated through the at least one lumen of catheter 201 in a direction indicated by arrow M until a distal end of catheter 204 is positioned adjacent the distal opening of guiding catheter 201, as generally depicted by FIG. 3A.

Figure 3B:
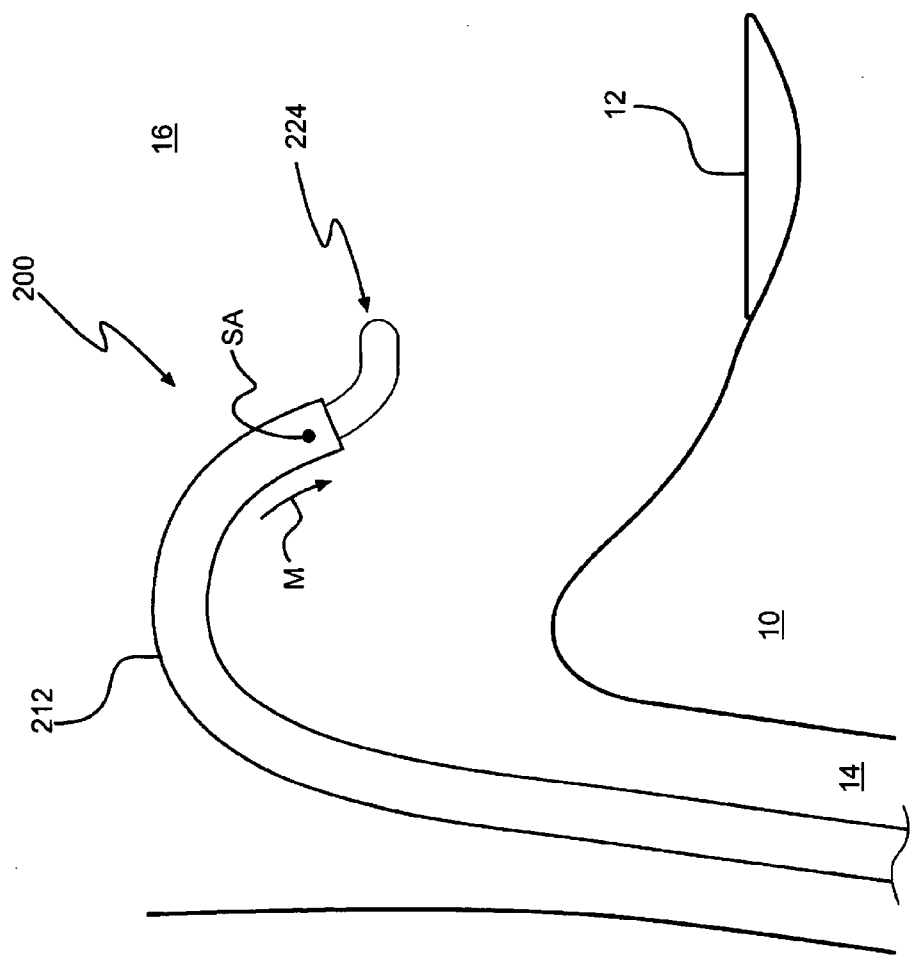
Figure 3C:
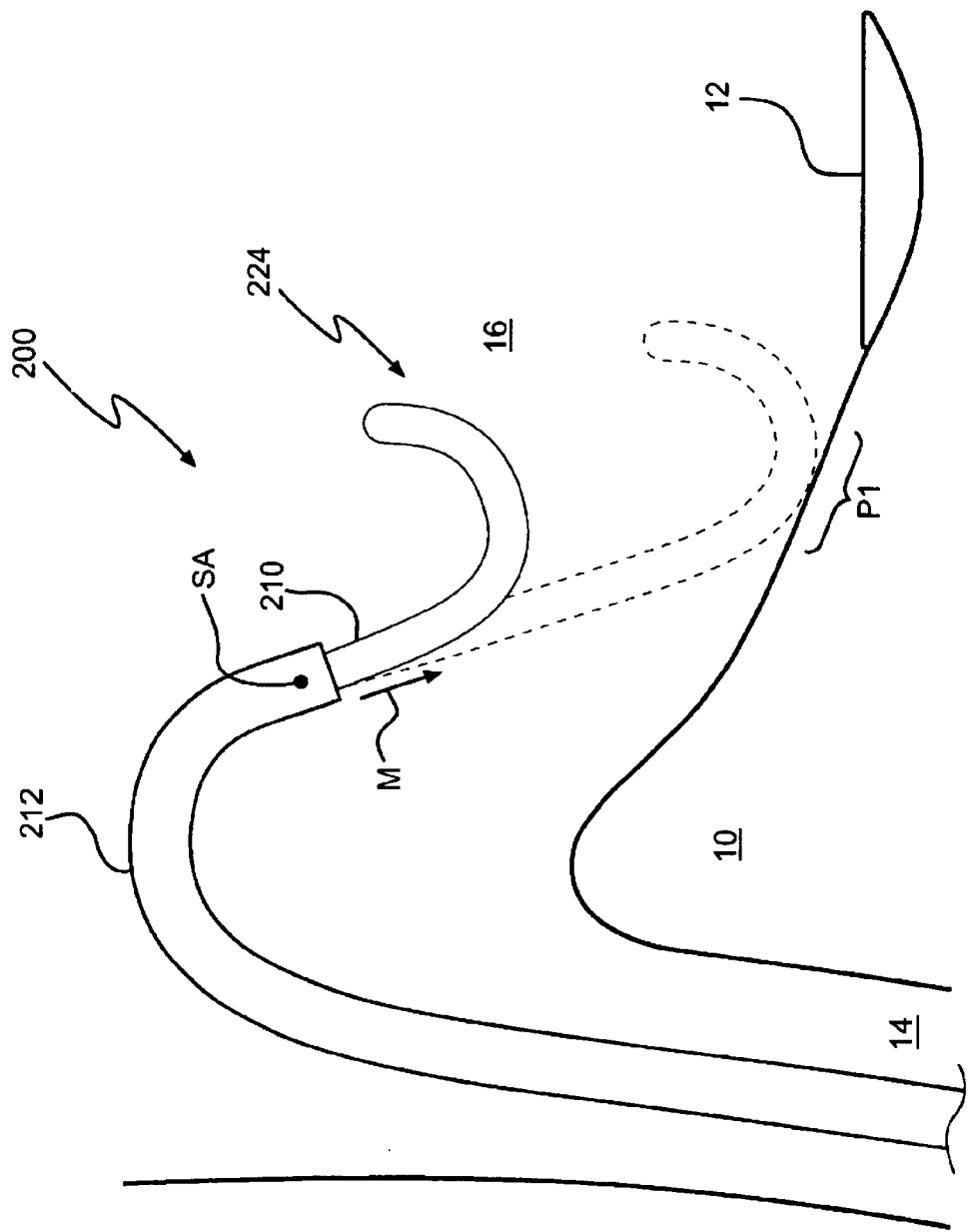

With reference also to FIG. 3B, once the guiding catheter 201 is properly positioned, the ablation catheter 204 is further advanced by operation of the advancement means by the user allowing the distal portion 224 to exit the distal opening of the guiding catheter 201. As depicted specifically in FIG. 3B, as the distal portion 204 exits guiding catheter 201, the support member 250 acts to deflect the distal portion 204 into a predetermined shape, as discussed above. With reference also to FIG. 3C, as the ablation catheter 204 is further advanced, the distal portion 224 further takes on the predetermined shape of support member 250 until the final shape is achieved. For illustrative purposes only, FIG. 3C depicts the distal portion 224 of ablation catheter 204 in a semi-circular shape. It should be apparent that other shapes can be selected, these shapes being directly based on the target tissue selected.

Once the distal portion 224 takes on its desired predetermined shape, the ablation catheter 204 is further advanced until at least a portion of distal portion 224 engages or is otherwise proximate to the target tissue. An exemplary position is shown in dashed line in FIG. 3C, distal portion 224 engages target tissue 10 generally at the position indicated by P1. The steering system 201 of guiding catheter 201 is further manipulated by the User to further move distal portion 224 across target tissue 10, creating intermediate lesions as part of a desired lesion path as further discussed above with respect to catheter system 100.

Now turning to FIGS. 4A and 4B, an exemplary catheter system 100A having a deflectable distal portion in accordance with the present invention will be discussed in greater detail. As stated above with respect to catheter 100, generally catheter 100A comprises elongated tubular member 110 having at least one lumen passing therethrough. The tubular member 110 ends in distal portion 124. As shown, distal portion 124 includes ablation device 130 comprising ablation element 136.

Figure 4A:
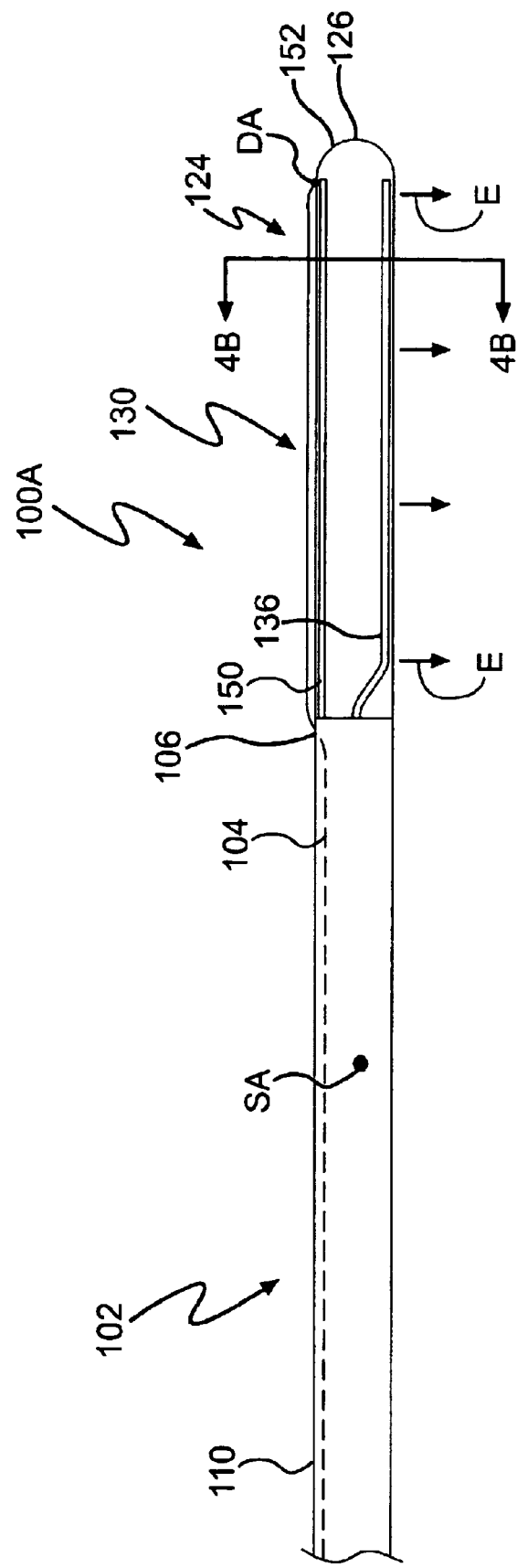
FIG. 4A is a side view of a first embodiment of an ablation system in accordance with the present invention.

In the embodiment of FIGS. 4A and 4B, ablation element 136 is a flexible antenna encased in an insulating material 134 adapted to emit electromagnetic energy radially about its structure over substantially its entire length, a portion of the radiated energy pattern generally depicted by arrows E. Insulating material 134 acts to hold ablation element 136 a fixed distance from the target tissue, tissue 10 for example, when the distal portion 124 contacts the tissue as depicted in FIGS. 2A and 2B. For the ablation device depicted, the insulator is a low-loss dielectric material able to transmit a substantial portion of ablative energy therethrough. Such materials may include, but are not limited to, TEFLON®, silicone, polyethylene, polyimide, or other materials having similar properties.

Ablation element 136 is coupled to a transmission medium adapted for transmission of ablative energy from an energy source, a microwave generator for example. The transmission medium may comprise, for illustration purposes only, a center conductor which is electrically coupled to a proximal end of ablation element 136, an outer conductor and an insulating material therebetween. For example, the transmission medium may be a coaxial cable adapted to transmit energy therethrough to ablation element 136 at predetermined power levels sufficient for ablating the target tissue. Additionally, for illustration purposes only, other exemplar modalities may include one or more optical fibers as part of a laser ablation system, metallic wires or coaxial cable for an ultrasound or RF ablation system, and tubular members having passages therethrough for fluid or gas agents utilized by cryogenic ablation systems.

It should be noted that the efficiency of ablation device 130 is related to, among other things, the ability of the transmission medium to effectively transmit energy from the energy source to ablation element 136. Therefore, ablation device 130 may further comprise elements which maximize the efficiency of the ablation system. For example, these elements may comprises one or more passive components which interface to one or more elements of the ablation system, comprising the energy source, transmission medium and ablation device, acting to match the impedance characteristics of, or otherwise tune, the ablation system itself.

While ablation element 136 is depicted as a linear antenna structure, any suitable structure can be used including, but not limited to, a helical antenna, an isolated monopole antenna, a lossy transmission line, or an exposed monopole antenna. The ablation element 136 can be formed from any suitable material including, but not limited to, spring steel, beryllium copper, or silver-plated copper. The diameter of ablation element 136 may be from about 0.005 to about 0.030 inches, and more preferably from about 0.013 to about 0.020 inches.

As shown, catheter 100A also includes pull wire 104 which has distal and proximal ends, the distal end operably attached to the handle portion (not shown) and the proximal end fixedly attached to the catheter 100A at or near a distal tip 126, designated as attachment point DA. The pull wire 104 exits the tubular member 110 at or near the distal portion 124 through opening 106 and travels along the exterior of member 110 to the attachment point DA, as discussed immediately above.

While FIGS. 4 and 5 depict pull wire 104 loosely placed within catheter 100, it should be apparent that pull wire 104 could be enclosed within a separate tubular member 104A (not shown). Member 104A would preferably run the length of catheter 100, the proximal end fixedly attached to the handle portion (not shown) and the distal end fixedly attached to catheter 100 structure. Alternatively, member 104A could be part of the outer catheter 100 structure, fixedly attached to and integral to the structure along the entire length of catheter 100. In this way, deflection forces associated with distal portion 124 can be transmitted directly to the handle portion, preventing undesirable deflection of catheter 100 and any tissue damage related thereto.

Distal portion 124 may optionally comprise a flexible support member 150. Support member 150 runs substantially the length of distal portion 124, with a proximal end of member 150 fixedly attached to catheter 100. Support member 150 preferably has a rectangular cross-section encouraging deflecting of the distal portion 124 along one plane. Support member 150 also acts to define a minimum radius of curvature to ensure consistent deflection of distal portion 124 along its length.

Figure 5A:
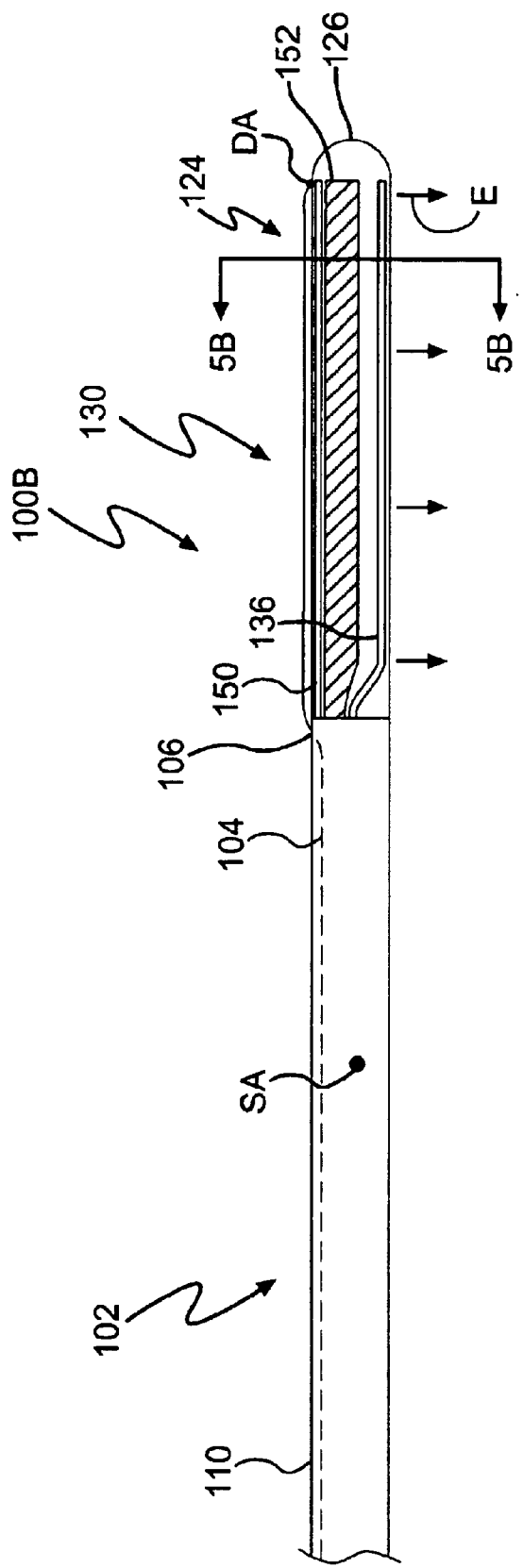
FIG. 5A is a side view of another embodiment of an ablation system in accordance with the present invention.
Figure 5B:
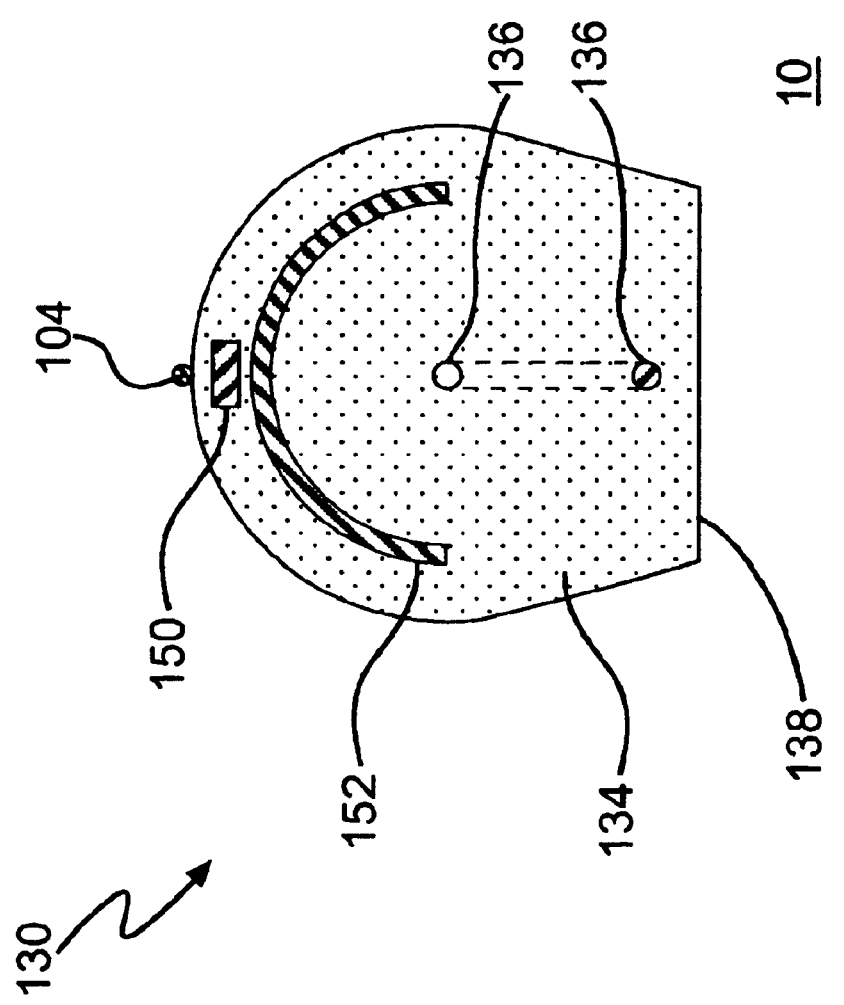
FIG. 5B is an end view of the ablation system of FIG. 4A.

With reference now to FIGS. 5A and 5B, another catheter system 100B shall be discussed. As depicted, the catheter system 100B is similar to system 100A except for distal portion 124. Distal portion 124 of catheter 100B further comprises a shielding means 152 adapted to shield surrounding tissue from ablative energy emitted therefrom. As discussed above, shielding means 152 may act to absorb ablative energy, microwave energy in this specific case, or reflect and redirect the ablative energy toward the target tissue to enhance ablation, reflection of the energy being a function of the construction material of shielding means 152 and redirection of the energy being a function of the geometric shape of shielding means 152. To facilitate absorption of the microwave energy, shielding means 152 may be formed from any suitable microwave absorption material with high loss tangent, such as a polymer filled with metallic powder for example. The geometric structure of shielding means 152 may define the resulting energy reflections to more precisely direct ablative energy toward target tissue.

With reference to FIGS. 5A and 5B, shielding means 152 acts to reflect at least a portion of the energy emitted by ablation element 136 toward target tissue, tissue 10 for example, resulting in more efficient ablation of the tissue. Furthermore, while shielding means 152 is shown having a curvilinear geometric shape, shielding means 152 may also be substantially planar in construction, formed from metallic foil for example. Alternatively, shielding means 152 may be constructed from a metallic wire mesh of copper, the wire mesh having wire spacing sufficient to prohibit passage of electromagnetic energy therethrough.

Figure 6A:
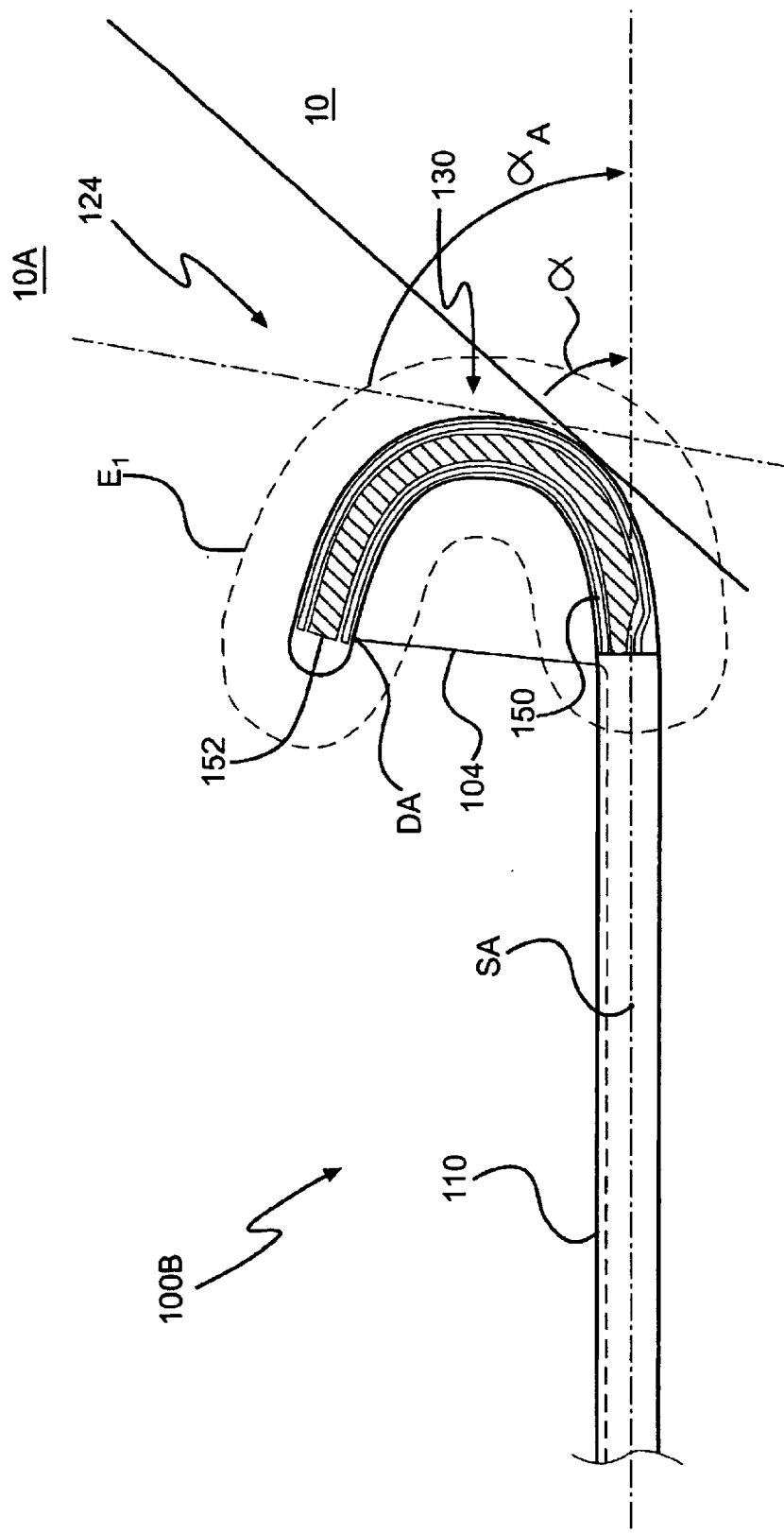
FIG. 6A is a side view of the ablation system of FIG. 5A shown with the distal end deflected to a first position.
Figure 6B:
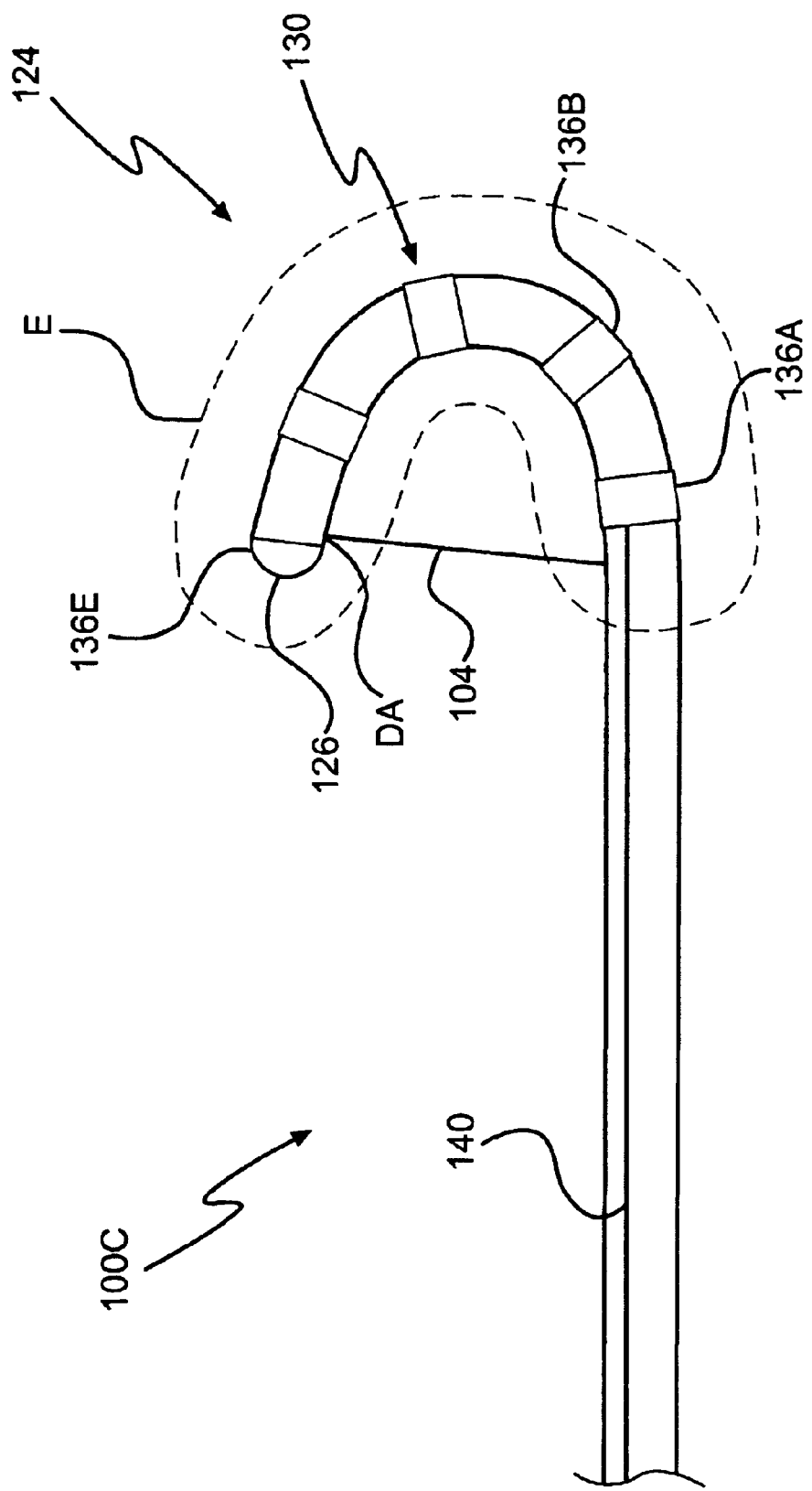
FIG. 6B is a side view of an ablation system incorporating an alternative ablation device, in accordance with the present invention.

With reference now to FIGS. 6A and 6B, catheter systems 100 having differing ablation devices 130 will be discussed. With specific reference to FIG. 6A, a catheter 100B is depicted having distal portion 124 comprising ablation device 130 similar to that depicted in FIGS. 5A and 5B. As shown, distal portion 124 is deflected to a first position through translation of pull wire 104. Once deflected, the ablation device 130 of catheter 100B emits an ablative energy pattern as depicted by area $E_1$. It should be understood, as with other depictions described herein, the energy pattern $E_1$ may be depicted in a planar view, such as in FIG. 6A, however, the ablative energy emitted has three-dimensional characteristics.

As discussed above, with the distal portion 124 deflected and the ablation device emitting energy as depicted by pattern $E_1$, the angle of approach $\alpha$ of catheter 100B becomes less significant. As described above, the longitudinal axis L of catheter member 110, which passes through attachment point A generally defines an attack angle $\alpha$ with respect to the target tissue, tissue 10 for example.

This advantage is more clearly understood when considering the distal portion engaging tissue 10A, the surface of tissue 10A shown in dashed line. Here, the approach angle $\alpha_A$, as defined in a similar fashion as immediately above. As depicted by the representative ablative energy pattern $E_1$, an equivalent amount of ablative energy is directed toward the target tissue 10, 10A, irregardless of the approach angle $\alpha$, $\alpha_A$, such that a desire ablation of the target tissue is performed. As clearly shown in FIG. 6A, ablation of tissue 10 is not directly dependent on the approach angle $\alpha$, $\alpha_A$.

Further translation of pull wire 104 results in further deflection of distal portion 124 to a second position shown in dashed line. With the distal portion 124 deflected to the second position a corresponding energy pattern $E_2$ is produced. The first and second position are exemplary positions depicting energy dispersion from between approximately 180° to about 270°. It should be understood, however, that energy dispersion ranges could vary from approximately 0° to about 270° with reference to the proximal end of portion 124, depending on the needs of the user, a surgeon for example. Additionally, it should be noted that while the ablation device 130 has been described as having a substantially circular configuration, other configurations are contemplated within the scope of the present invention to allow the User to ablate tissues of differing geometries.

While the ablation device 130 of the catheter 100B embodiment comprises support member 150, the shielding device 152 may be adapted to control the geometry of deflection with respect to the distal portion 124. Additionally, as stated above, the shielding means 152 may be configured such that the flexibility changes along its longitudinal axis resulting in different geometric configurations when distal portion 124 is deflected.

Now turning to FIG. 6B, catheter 100C incorporating an alternative ablation device is shown. Catheter 100C has a distal portion 124 including an ablation device comprising at least one radio frequency (RF) electrode 136A–E operably controlled by the User through controlling means 140. The electrodes 136A–E of ablation device 130 define an energy pattern depicted by E, shown in dashed line. Controlling means 140 controls the application of energy to the electrodes 136A–E, either alone, as a group of one or more, or the entire group. For example, controlling means 140 of catheter 100C may comprise one or more electrically conductive wires operably connected to electrodes 136A–E and the handle portion (not shown). The User would apply ablative energy to target tissue through the direction of energy through one or more electrodes 136A–E via controlling means 140.

It is important to note that the depiction of energy dispersions discussed herein do not take into account the efficiency of the different modalities disclosed herein. The energy patterns described herein are for discussion purposed only. It should be clear from the discussion herein that the energy emitted from the ablation element(s) will impact target tissue in an equivalent manner, without respect to an approach angle $\alpha$ as defined herein.

Note that the ablation device 130 of distal portion 124 of catheter 100C, may comprise more or less RF electrodes further defining an appropriate energy pattern E. Furthermore, the RF electrodes 136A–E may be in the form of a coiled spring such that the RF electrodes themselves may individually deflect as the distal portion 124 deflects. While the RF electrodes are shown in a spaced-apart relationship with respect to each other, electrodes 136A–E may be positioned in close proximity with respect to each other, further defining energy dispersion. Additionally, each RF electrode 136A–E may be controlled separately through control means 140, further controlling or defining the energy dispersion area. The electrodes 136A–E may be semi-circular defining an energy pattern which is directed 180° about the longitudinal axis of the device, essentially defining a side-firing device which, when the distal portion is deflected, can transform partially or totally into a distal firing device.

While the above procedure is described in terms of three lesions, the actual number of overlapping lesions is a function of the ablative energy utilized and the configuration of distal portion 124, comprising ablative device 130. For example, the length of any intermediate lesion created is a direct function of the dimensional characteristics of the ablation device utilized. Therefore, the desired resultant long continuous lesion may comprise the creation of fewer or greater intermediate lesions than described above.

As discussed in more detail above, ablation device 130 may also include an energy shielding means adapted to be opaque to the ablative energy utilized, such that, tissue adjacent to target tissue 10, for example, is protected from the ablative energy. Furthermore, is should be noted that the energy shielding means can be further adapted to reflect the ablative energy in a predetermined and desirable fashion as to focus the ablative energy at a desired region of the target tissue 10, whereby the lesion characteristics can be better controlled.

For example, considering the ablative element of FIGS. 5A & 5B, the shielding means may be formed to reflect and direct microwave energy in a relatively thin line along the longitudinal axis of the antenna, resulting in the desired formation of a relatively thin long intermediate lesion. Alternatively, the shielding means of a cryo based system may be constructed from thermal isolating material, the shielding means 152 axially surrounding a substantial portion of ablative device 130 leaving only a relatively thin opening along the longitudinal axis of device 130, corresponding to a desired lesion. The opening would be controllably directed toward target tissue 10, as discussed above, to create an intermediate lesion. Additionally, steering system 102 may be constructed as to limit the deflection of intermediate portion 118 to one plane, ensuring, for example, that the opening of the cryo-based ablation device 130, discussed immediately above, is directed toward target tissue 10.

While the ablative device 130 is preferably adapted to emit microwave energy sufficient to ablate the target tissue upon which a lesion is desired, other ablative energies utilized by an ablative device 130 in catheter 100 may include, but is not limited to, one or more of the following energies, along or in combination: microwave energy, laser energy or other forms of light energy in both the visible and nonvisible range, radio frequency (RF) energy, ultrasonic energy, cryogenic energy, chemical agent, thermal energy, or any other energy which can be controllably emitted and directed at least towards a portion of a desired target tissue, transporting ablation energy to the target tissue at sufficient energy levels resulting in tissue ablation and corresponding lesion formation.

One exemplary ablation device 130 comprises a monopole microwave antenna as disclosed and further described in commonly owned U.S. Pat. No. 6,277,113, entitled "Monopole Tip for Ablation Catheter and Methods for Using Same," which is hereby incorporated herein by reference, in its entirety. Alternatively, ablation device 130 may comprise other microwave antenna structures as disclosed and further described in commonly owned U.S. Pat. No. 6,245,062, entitled "Directional Reflector Shield Assembly for a Microwave Ablation Instrument," U.S. patent application Ser. No. 09/484,548, filed Jan. 18, 2000, entitled "Microwave Ablation Instrument With Flexible Antenna Assembly and Method", and U.S. patent application Ser. No. 09/751,472, filed Dec. 28, 2000, entitled "A Tissue Ablation Apparatus with a Sliding Ablation Instrument and Method," all hereby incorporated herein by reference, each in its entirety.

Additionally, catheter 100 may further comprise one or more electrodes strategically placed upon the distal portion 124 to facilitate capture of certain electrophysiological signals. Such signals allow a User to determine tissue characteristics of a target tissue site and also provide confirmation that the distal portion 124 is properly positioned substantially proximal and parallel to a target tissue, for example. Such electrode arrangement systems may be similar to those disclosed in U.S. patent application Ser. No. 09/548,331, filed Apr. 12, 2000, entitled "Electrode Arrangement for Use in A Medical Instrument," hereby incorporated herein by reference, in its entirety.

While the present invention has been primarily described with respect to tissue ablations within the right atrium of the heart, it will be appreciated that the ablation systems disclosed herein may just as easily be applied to ablation of other tissues, such as the tissue surrounding the sinus cavities for example. The tissue ablations may be performed through either open surgery techniques or through minimal invasive techniques.

Although the foregoing invention has been described in some detail for purposes of clarity of understanding, it will be apparent that certain changes and modifications may be practiced within the scope of the appended claims.

What is claimed is:

1. A method of ablating tissue with an ablation apparatus including an elongated member having a longitudinal axis extending between a proximal end and a configurable distal portion that includes an ablation element disposed to emit ablative energy, the method comprising the steps of:

advancing the distal portion into a patient's body toward a target tissue site;

configuring the distal portion in a selected shape that is skewed relative to the longitudinal axis;

deflecting the elongated member intermediate the proximal end and the configured distal portion to position the configured distal portion toward the target tissue site;

advancing the configured distal portion to contact the target tissue;

additionally deflecting the elongated member intermediate the proximal end and the configured distal portion to move the configured distal portion along an extended path at the target tissue site; and applying ablative energy to the ablative element during the additional deflecting to ablate tissue along the extended path.

2. The method according to claim 1 wherein configuring the distal portion includes forming the distal portion into a curvilinear selected shape lying in a plane.

3. The method according to claim 2 wherein deflecting the elongated member occurs substantially within said plane.

4. The method according to claim 3 wherein the additional deflecting occurs substantially within said plane.

5. The method according to claim 3 wherein the curvilinear selected shape extends along one rotational direction within the plane and the deflecting of the elongated member extends along the longitudinal axis in an opposite rotational direction substantially within said plane to position the curvilinear distal portion for contacting tissue at the target site.

6. The method according to claim 5 in which the ablative element emits ablative energy along a convex peripheral portion of the curvilinear selected shape substantially aligned with the plane.

7. The method according to claim 2 wherein the curvilinear selected shape is a portion of a substantially circular configuration.

8. The method according to claim 7 wherein the portion of the substantially circular configuration has a radius in the range between about 0.5 cm and about 5 cm.

9. The method according to claim 1 wherein the additional deflecting occurs substantially simultaneously with applying ablative energy for forming a substantially continuous extended path of ablated tissue.

* * * * *